Figure 1:
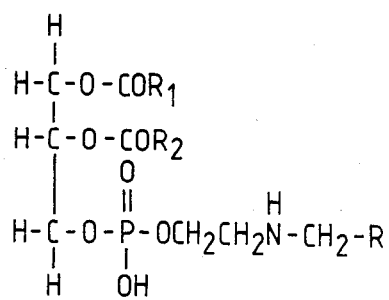

United States Patent [19]

Todt et al.

[11] Patent Number: 4,547,387

[45] Date of Patent: Oct. 15, 1985

[54] EDIBLE EMULSIONS CONTAINING AMADORI REARRANGEMENT PRODUCTS

[75] Inventors: Klaus H. Todt, Hamburg, Fed. Rep. of Germany; Wilhelmus A. M. Castenmiller, Vlaardingen, Netherlands

[73] Assignee: Lever Brothers Company, New York, N.Y.

[21] Appl. No.: 501,743

[22] Filed: Jun. 6, 1983

[30] Foreign Application Priority Data

Jun. 8, 1983 [GB] United Kingdom ............ 8216630

[51] Int. Cl.$^4$ ........................ A23D 3/00; A23D 3/02
[52] U.S. Cl. .................... 426/602; 426/604; 426/611
[58] Field of Search ............ 426/601, 602, 603, 604, 426/611, 612, 613, 662

[56] References Cited

U.S. PATENT DOCUMENTS

| | | | |
|---|---|---|---|
| 2,629,662 | 2/1953 | Julian et al. | 426/662 |
| 3,004,922 | 10/1961 | Buer. | |
| 3,652,397 | 3/1972 | Pardun | 426/603 X |
| 3,663,235 | 5/1972 | Menz et al. | 426/604 |
| 3,690,894 | 9/1972 | Kelly et al. | 426/662 X |
| 3,940,423 | 2/1976 | Eibl et al. | 426/604 X |
| 4,399,224 | 8/1983 | Flider et al. | 426/662 X |
| 4,425,334 | 1/1984 | Hunt. | |

FOREIGN PATENT DOCUMENTS

| | | | |
|---|---|---|---|
| 417552 | 10/1934 | United Kingdom. | |
| 815246 | 6/1959 | United Kingdom. | |
| 952848 | 3/1964 | United Kingdom | 426/604 |

*Primary Examiner*—Robert Yoncoskie
*Attorney, Agent, or Firm*—Lynne Darcy; James J. Farrell

[57] ABSTRACT

A process for producing a stabilized, edible water- and oil-containing emulsion, particularly a margarine with a low level of salt with a reduced tendency to spatter during frying, comprising dispersing or dissolving in either the aqueous or the fatty phase an Amadori rearrangement product derived from phosphatidyl ethanolamine and a reducing sugar.

6 Claims, 2 Drawing Figures

EDIBLE EMULSIONS CONTAINING AMADORI REARRANGEMENT PRODUCTS

The present invention relates to new Amadori rearrangement products, to a process for producing said products and to their use as stabilizing agents, particularly anti-spattering agents for edible water- and oil-containing emulsions, particularly W/O emulsions of the margarine-type.

In the initial stage of the frying process, margarines separate essentially into an aqueous phase and an oil phase. When the temperature is increased above the boiling point of water, spattering occurs since the water evaporates vigorously entraining some of the oil phase.

Phosphatides such as mixtures of phosphatidyl choline, phosphatidyl ethanolamine, phosphatidyl inositol, originating from egg-yolk, soyabeans, rapeseed, maize and the like have been used as emulsifiers and anti-spattering agents in margarines. However, phosphatides are less active in the absence of sodium chloride or in the presence of very low levels (e.g. 0.4% or less) of sodium chloride. Attempts have been made by the Applicants to improve the anti-spattering activity of phosphatides; these attempts resulted in the development of expensive purification methods and in the development of lysophosphatides i.e. partially hydrolyzed phosphatides. These partially hydrolyzed phosphatides are very effective anti-spattering agents but sometimes develop a bitter off-flavour.

Applicants have found new Amadori rearrangement products which are very effective anti-spattering agents in W/O emulsion spreads, even in emulsions wherein salt (sodium chloride) is absent or is present in very low concentrations, e.g. 0.4%. The new Amadori rearrangement products according to the invention display also good emulsifying properties in O/W emulsions.

The new products according to the invention are represented in FIG. 1, wherein $R_1$ and $R_2$ are identical or different, saturated or unsaturated fatty acid residues and R is a sugar moiety. $R_1$ and $R_2$ are preferably fatty acid residues generally occurring in the phosphatidyl-ethanolamine (PE) molecules as found in nature, which comprise fatty acid residues having 16–26 C-atoms, predominantly consisting of linoleic acid-, oleic acid- and palmitic acid-residues. The sugar moiety generally consists of a carbohydrate carrying a carbonyl group, stemming e.g. from lactose, glucose, fructose or an oligosaccharide obtained by hydrolysis of starch (starch hydrolysate). Preferably the sugar moiety stems from lactose.

Figure 2:
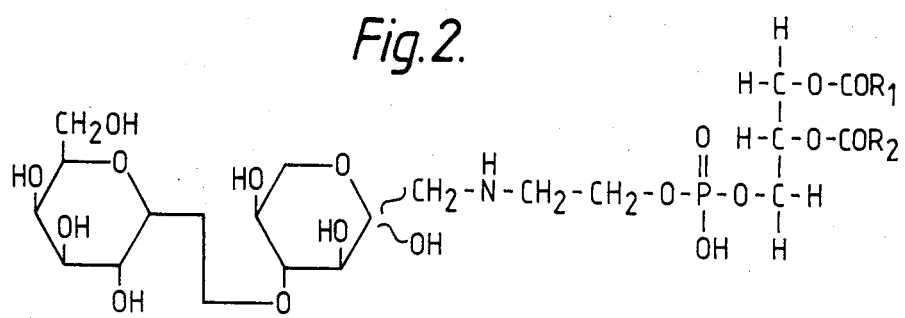

The stucture of the preferred product according to the invention, which is derived from PE and lactose, is illustrated in FIG. 2.

The new Amadori rearrangement products according to the invention are produced according to a process comprising allowing phosphatidyl-ethanolamine or a mixture of phosphatides which contains phosphatidyl-ethanolamine, to react with a carbohydrate carrying a carbonyl group, i.e.a source of a reducing sugar, at a temperature ranging from 70° to 135° C. under substantially moisture-free conditions.

Above 135° C. substantial degradation of the reaction product takes place. Below 70° C. the conversion will take too long to proceed. The reaction is therefore preferably carried out at a temperature ranging from 80° to 115° C.

The reaction is preferably carried out under moisture-free conditions, i.e. in a medium containing less than 5% water and preferably less than 2% water for a period which may vary from a few minutes to a few hours, e.g. 1–3 hours, preferably in the absence of a solvent. Although it is possible to allow the reactants to react in the form of a dispersion in oil or in a mixture of solvents such as dimethylsulfoxide and chloroform, or triethylamine and dimethylformamide, the reaction in these cases is markedly slower.

When the reaction is carried out in the absence of a solvent it is important to ensure that the phosphatide mixture and the carbohydrate (reducing-sugar-containing material) have a large contact area.

The preferred starting material for the reaction is therefore produced by spray-drying in warm air a mixture of said phosphatides with e.g. milk solids.

Applicants have found that the best conversion rates are observed when both materials are present as a spray-dried mixture.

The reducing sugar preferably consists of lactose, but may comprise mixtures of lactose and another reducing sugar such as glucose or fructose.

A suitable source for the reducing sugar may consist of milk solids such as skimmilk powder, whey powder and the like, preferably in the form of a finely divided powder such as a spray-dried powder.

A preferred reaction mixture consists of a spray-dried mixture containing 35–55 wt.% phosphatides and 45 to 65 wt.% milk solids.

In the process of the present invention a crude or a purified mixture of phosphatides from soyabeans is preferably used, because it is readily available and relatively cheap. Soybeans contain considerable proportions of phosphatides (phosphatidyl-choline, phosphatidyl-ethanolamine and phosphatidyl-inositol being the most important), which are separated from the oil after the extraction of oil with a solvent. On introduction of water or steam into the oil after evaporation of the solvent, the phosphatides swell up and separate from the oil. After the bulk of the oil has been removed, a sediment remains which consists of phosphatides, oil and a minor quantity of water.

According to the present invention edible water- and oil-containing emulsions, particularly W/O emulsion-spreads of the margarine type having good frying properties and a reduced tendency to spattering are provided which contain the new Amadori rearrangement products according to the invention.

Such emulsions can be produced by dispersing the Amarori rearrangement products either in the aqueous or in the fatty phase in a proportion preferably ranging from 0.05–5 wt.%, based on the total composition.

The above emulsion can also be produced by incorporating in either the aqueous phase or the fatty phase an effective proportion of a product obtained by reacting a mixture of phosphatides containing phosphatidyl-ethanol-amine with a reducing-sugar-containing material as hereinbefore described.

The invention will now be illustrated in the following examples.

EXAMPLE 1

A spray-dried mixture consisting of 45 wt.% of a mixture of soyphosphatides and 55 wt.% milk solids was heated for about 1½ hours at about 100° C. in the absence of solvent.

The milk solids contained about 45% lactose and about 9% casein. The reaction was considered as completed when analysis of the reaction product by thin layer chromatography, using Kieselgel-Fertigplatten (Merck) and a mixture of $CHCl_3$:acetone:$CH_3OH$:acetic acid:water in the following ratio: 10:4:2:2:1, demonstrated that the spot corresponding to phosphatidyl-ethanolamine had disappeared and that a new spot corresponding to that of the Amadori product according to FIG. 2 appeared, below the spots corresponding to phosphatidyl-choline and phosphatidyl-ethanolamine. The new spot gave a positive colour reaction with the Zinzadze reagent for P, a negative reaction for primary amino groups, a positive reaction to sugars (anisaldehyde/$H_2SO_4$) and showed strong reducing properties typical for Amadori rearrangement compounds with alkaline o-dinitrobenzene, alkaline triphenyltetrazoliumchloride, $AgNO_3$.

The product could not be hydrolyzed in 0.1N HCl and on cleavage with $HJO_4$ the phosphatidyl-ethanolamine spot was regenerated.

About 0.5 wt.% of the product of the reaction was incorporated in saltless (sodiumchloride-free) margarine comprising 84% fat and 16% of an aqueous phase, by dispersing it in the fatty phase.

The margarine obtained was used for shallow frying in a pan and the spattering behaviour was tested.

The spattering behaviour on heating was found very satisfactory.

A comparative experiment was carried out in which an unreacted, non-heated mixture of the same phosphatides and milk solids was incorporated in the same margarine and the spattering behaviour was tested. This test showed the superiority of the product according to the present invention.

The spattering behaviour was observed and measured as follows:

25 g of margarine are heated in a glass pan on a hot plate. A filter paper is placed over the pan; the distance between the bottom of the pan and the paper is 25 cm.

The frying test is carried out for about 8 minutes.

Immediately after the test the paper is visually assessed for the degree of spattering (amount of spattered fat).

EXAMPLE 2

A mixture consisting of 0.75 parts of phosphatidylethanolamine and 3.0 parts of lactose was dissolved in a solvent mixture consisting of 15 ml dimethyl formamide and 1 ml triethylamine.

The solution was heated for 8 hours at 70° C. The solvent was removed by evaporation. The excess of lactose was removed using a mixture of chloroform, methanol and water. The isolated, purified product (Amadori-rearrangement product) was then subjected to thin-layer chromatography and to the tests as described in Example 1. Identical results were obtained. The product of the reaction when tested for its anti-spattering properties at a level of about 0.1% by weight in a saltless margarine gave excellent results.

The anti-spattering properties of a saltless margarine containing the product of the invention were compared to the anti-spattering properties of saltless margarines containing:

an unreacted mixture (a) of phosphatidyl-ethanolamine and lactose or a mixture (b) of soy phosphatides in its native form or a mixture (c) consisting of soy lecithin hydrolyzed with phospholipase A.

The anti-spattering properties of the saltless margarine containing the Amadori rearrangement product according to the invention were superior to those displayed by the saltless margarines containing mixture (a) or (b) and were comparable to those achieved by using mixture (c).

The margarine containing the Amadori rearrangement product according to the invention had excellent organoleptic properties and no bitter taste could be perceived, whereas the margarine containing mixture (c) had a somewhat bitter taste.

EXAMPLE 3

In this example the use of the product according to the invention as an emulsifier for O/W emulsions is shown.

An O/W emulsion (A) of the following composition was prepared:

| Ingredient | % by weight |
| --- | --- |
| Soybean lecithin reacted with glucose in dimethylformamide and triethylamine or a lipid extract of a heated spray-dried powder according to Ex. 1 | 0.3 |
| Fat | 2.7 |
| Skimmilk powder/whey powder (2:1 mixture) | 10.0 |
| Water up to | 100. |

For comparison a similar emulsion (B) was produced in the same way but using soybean lecithin instead of the product according to the invention.

The stability of both emulsions was tested in glass cylinders in which the emulsions were allowed to stand for several hours, by observing the degree of phase separation.

The stability of the O/W emulsion containing the Amadori rearrangement product according to the invention was found to be superior.

We claim:

1. A process for producing a stabilized water- and oil-containing edible emulsion, comprising dispersing or dissolving in either the aqueous or the fatty phase 0.05–5 wt. % of an Amadori rearrangement product having the structure:

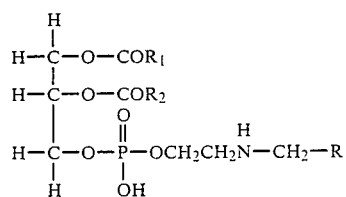

wherein $R_1$ and $R_2$ are identical or different, saturated or unsaturated fatty acid residues and R is a reducing carbohydrate selected from the group consisting of glucose, fructose, lactose and an oligosaccharide obtained by hydrolysis of starch.

2. A process according to claim 1, wherein the emulsion is a water-in-oil emulsion spread of the margarine-type.

3. A process according to claim 2, wherein the water-in-oil emulsion spread of the margarine type contains 0–0.4% of sodium chloride.

4. Water- and oil-containing edible emulsion containing 0.05–5 wt % of an Amadori rearrangement product having the structure:

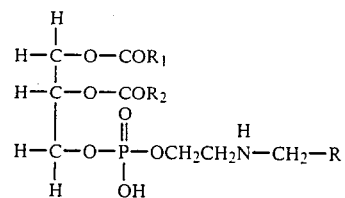

wherein $R_1$ and $R_2$ are identical or different, saturated or unsaturated fatty acid residues and R is a reducing carbohydrate selected from the group consisting of glucose, fructose, lactose and an oligosaccharide obtained by hydrolysis of starch.

5. Water- and oil-containing edible emulsion according to claim 4, wherein said emulsion is a margarine.

6. Margarine according to claim 5, which contains 0–0.4% of sodium chloride.